United States Patent [19]
Hohlweg et al.

[11] Patent Number: 6,017,915
[45] Date of Patent: Jan. 25, 2000

[54] HETEROCYCLIC COMPOUNDS

[75] Inventors: Rolf Hohlweg, Kvistgaard; Tine Krogh Jørgensen, Ølstykke; Knud Erik Andersen, Smørum; Uffe Bang Olsen, Vallensbaek; Peter Madsen, Bagsvaerd, all of Denmark; Zdenék Polivka, Praha, Czech Rep.; Otylie Königová, Praha, Czech Rep.; Frantisek Miksik, Praha, Czech Rep.; Martina Kovandová, Praha, Czech Rep.; Alexandra Silhánková, Praha, Czech Rep.; Karel Sindelár, Praha, Czech Rep.

[73] Assignee: Novo Nordisk A/S, Bagsvaerd, Denmark

[21] Appl. No.: 09/079,599

[22] Filed: May 15, 1998

Related U.S. Application Data

[62] Division of application No. 08/715,665, Sep. 18, 1996, Pat. No. 5,753,678.

[30] Foreign Application Priority Data

Sep. 19, 1995 [DK] Denmark ................................ 1040/95
Sep. 19, 1995 [DK] Denmark ................................ 1041/95

[51] Int. Cl.$^7$ ...................... A61K 31/535; C07D 413/06; C07D 413/12
[52] U.S. Cl. ...................... 514/232.8; 544/148; 544/375; 540/575; 514/218; 514/253

[58] Field of Search .................. 514/255, 232.8, 514/218, 253; 544/375, 148; 540/575

[56] References Cited

U.S. PATENT DOCUMENTS 4,229,350  10/1980  Rozsa et al. .......................... 260/243.3

FOREIGN PATENT DOCUMENTS 2833892  2/1979  Germany .
3643991  6/1987  Germany .
3844394  7/1989  Germany .

OTHER PUBLICATIONS

Kálman, A., et al. Acta Biochim. Biophys. Hung., vol. 24, Nos. 1–2, pp. 143–158 (1989).

*Primary Examiner*—John Kight
*Assistant Examiner*—Charanjit S. Aislakh
*Attorney, Agent, or Firm*—Steve T. Zelson; Carol E. Rozek

[57] ABSTRACT

The present invention relates to novel N-substituted amino alcohols, amino acids and acid derivatives thereof in which a substituted alkyl chain forms part of the N-substituent or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation.

5 Claims, No Drawings

HETEROCYCLIC COMPOUNDS

CROSS-REFERENCE TO RELATED APPLICATIONS

This application is a divisional of U.S. application Ser. No. 08/715,665 filed Sep. 18, 1996 and claims priority under 35 U.S.C. 119 of Danish application Ser. Nos. 1040/95 and 1041/95 filed Sep. 19, 1995, the contents of which are fully incorporated herein by reference, now U.S. Pat. No. 5,753,678.

FIELD OF THE INVENTION

The present invention relates to novel N-substituted amino alcohols, amino acids and acid derivatives thereof in which a substituted alkyl chain forms part of the N-substituent or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation.

The invention also relates to the use of the present compounds for the treatment of insulin resistance in non-insulin-dependent diabetes mellitus (NIDDM) or ageing, the present compounds knowing to interfere with neuropeptide containing C-fibres and hence inhibit the secretion and circulation of insulin antagonizing peptides like CGRP or amylin.

BACKGROUND OF THE INVENTION

The nervous system exerts a profound effect on the inflammatory response. Antidromic stimulation of sensory nerves results in localized vasodilation and increased vascular permeability (Janecso et al. Br. J. Pharmacol. 1967, 31, 138–151) and a similar response is observed following injection of peptides known to be present in sensory nerves. From this and other data it is postulated that peptides released from sensory nerve endings mediate many inflammatory responses in tissues like skin, joint, urinary tract, eye, meninges, gastro-intestinal and respiratory tracts. Hence inhibition of sensory nerve peptide release and/or activity, may be useful in treatment of, for example arthritis, dermatitis, rhinitis, asthma, cystitis, gingivitis, thrombophlebitis, glaucoma, gastro-intestinal diseases or migraine.

Further, the potent effects of CGRP on skeletal muscle glycogen synthase activity and muscle glucose metabolism, together with the notion that this peptide is released from the neuromuscular junction by nerve excitation, suggest that CGRP may play a physiological role in skeletal muscle glucose metabolism by directing the phosphorylated glucose away from glycogen storage and into the glycolytic and oxidative pathways (Rossetti et al. Am. J. Physiol. 264, E1–E10, 1993). This peptide may represent an important physiological modulator of intracellular glucose trafficking in physiological conditions, such as exercise, and may also contribute to the decreased insulin action and skeletal muscle glycogen synthase in pathophysiological conditions like NIDDM or ageing-associated obesity (Melnyk et al. Obesity Res. 3, 337–344, 1995) where circulating plasma levels of CGRP are markedly increased. Hence inhibition of release and/or activity of the neuropeptide CGRP may be useful in the treatment of insulin resistance related to type 2 diabetes or ageing.

In U.S. Pat. No. 4,383,999 and U.S. Pat. No. 4,514,414 and in EP 236342 as well as in EP 231996 some derivatives of N-(4,4-disubstituted-3-butenyl)azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as GABA uptake inhibitors. EP 221572 claims that 1-aryloxyalkylpyridine-3-carboxylic acids are inhibitors of GABA uptake.

In DE 2833892 some 12H-dibenzo[d,g][1,3,6] dioxozocine derivatives are claimed as local anaesthetics or for treatment of parkinsonism.

DESCRIPTION OF THE INVENTION

The present invention relates to novel N-substituted amino alcohols, amino acids and acid derivatives thereof of formula I

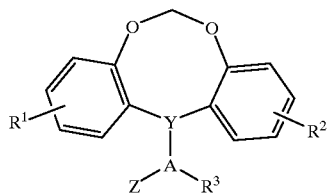

wherein $R^1$ and $R^2$ independently are hydrogen, halogen, trifluoromethyl, hydroxy, $C_{1-6}$-alkyl or $C_{1-6}$-alkoxy; and
$R^3$ is hydrogen or $C_{1-3}$-alkyl; and
A is $C_{1-3}$-alkylene; and
Y is >CH—$CH_2$—, >C=CH—, >CH—O—, >C=N—, >N—$CH_2$— wherein only the underscored atom participates in the ring system; and
Z is selected from

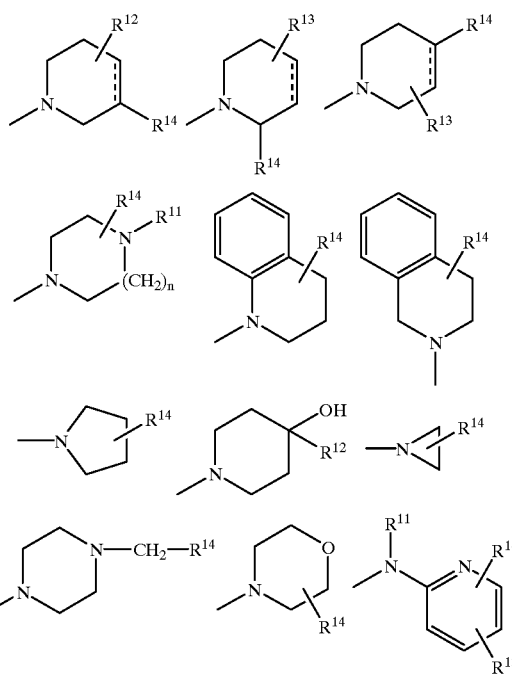

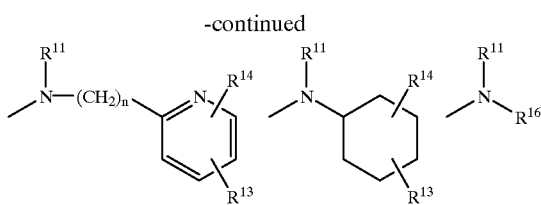

wherein n is 1 or 2; and
$R^{11}$ is hydrogen or $C_{1-6}$-alkyl; and
$R^{12}$ is hydrogen, $C_{1-6}$-alkyl, $C_{1-6}$-alkoxy or phenyl optionally substituted with halogen, trifluoromethyl, hydroxy, $C_{1-6}$-alkyl or $C_{1-6}$-alkoxy; and
$R^{13}$ is hydrogen, halogen, trifluoromethyl, hydroxy, $C_{1-6}$-alkyl or $C_{1-6}$alkoxy; and
$R^{14}$ is —$(CH_2)_m$OH or —$(CH_2)_t COR^{15}$ wherein m is 0, 1, 2, 3, 4, 5 or 6 and t is 0 or 1 and
wherein $R^{15}$ is —OH, $NH_2$, —NHOH or $C_{1-6}$-alkoxy; and
$R^{16}$ is $C_{1-6}$-alkyl or —B—$COR^{15}$, wherein B is $C_{1-6}$-alkylene, $C_{2-6}$-alkenylene or $C_{2-6}$-alkynylene and $R^{15}$ is the same as above; and
... is optionally a single bond or a double bond;
or a pharmaceutically acceptable salt thereof.

The compounds of formula I may exist as geometric and optical isomers and all isomers and mixtures thereof are included herein. Isomers may be separated by means of standard methods such as chromatographic techniques or fractional crystallisation of suitable salts.

Preferably, the compounds of formula I exist as the individual geometric or optical isomers.

The compounds according to the invention may optionally exist as pharmaceutically acceptable acid addition salts or—when the carboxylic acid group is not esterified—as pharmaceutically acceptable metal salts or—optionally alkylated—ammonium salts.

Examples of such salts include inorganic and organic acid addition salts such as hydrochloride, hydrobromide, sulphate, phosphate, acetate, fumarate, maleate, citrate, lactate, tartate, oxalate or similar pharmaceutically acceptable inorganic or organic acid addition salts, and include the pharmaceutically acceptable salts listed in Journal of Pharmaceutical Science, 66, 2 (1977) which are hereby incorporated by reference.

The term "$C_{1-6}$-alkyl" as used herein, alone or in combination, refers to a straight or branched, saturated hydrocarbon chain having 1 to 6 carbon atoms such as e.g. methyl, ethyl, n-propyl, isopropyl, n-butyl, sec-butyl, isobutyl, tert-butyl, n-pentyl, 2-methylbutyl, 3-methylbutyl, n-hexyl, 4-methylpentyl, neopentyl, n-hexyl, 1,2-dimethylpropyl, 2,2-dimethylpropyl and 1,2,2-trimethylpropyl.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "halogen" means fluorine, chlorine, bromine or iodine.

Illustrative examples of compounds encompassed by the present invention include:
2-Chloro-12-(3-dimethylamino)propylidene-12H-dibenzo[d,g][1,3]dioxocine
2,10-Dichloro-12-(2-dimethylamino)ethoxy-12H-dibenzo[d,g][1,3]dioxocine.
2,10-Dichloro-12-(3-dimethylamino)propyl-12H-dibenzo[d,g][1,3]dioxocine
2,10-Dichloro-12-(3-dimethylamino-1-methyl)ethoxy-12H-dibenzo[d,g][1,3]dioxocine
3-Chloro-12-(2-dimethylaminopropylidene)-12H-dibenzo[d,g][1,3]dioxocine
3-Chloro-12-(3-dimethylamino)propylidene-12H-dibenzo[d,g][1,3]-dioxocine
3-Chloro-12-(3-dimethylamino-1-methylpropylidene)-12Hdibenzo-[d,g][1,3]-dioxocine
2-Fluoro-12-(3-dimethylamino)propylidene-12H-dibenzo[d,g][1,3]dioxocine
2-Methyl-12-(3-(4-methyl-1-piperazinyl)propylidene)-12H-dibenzo[d,g][1,3]dioxocine
2-Chloro-12-(3-(4-methyl-1-piperazinyl)propylidene)-12H-dibenzo[d,g][1,3]dioxocine
3-Chloro-12-(3-(4-methyl-1-piperazinyl)propylidene)-12H-dibenzo[d,g][1,3]-dioxocine
1-(3-(12H-Dibenzo[d,g][1,3]dioxocin-12-ylidene)propyl)-3-piperidinecarboxylic acid ethylester
1-(3-(12H-Dibenzo[d,g][1,3]dioxocin-12-ylidene)propyl)-3-piperidinecarboxylic acid
or a pharmaceutically acceptable salt thereof.

As used herein, the term "patient" includes any mammal which could benefit from treatment of neurogenic pain or inflammation or insulin resistance in NIDDM. The term particularly refers to a human patient, but is not intended to be so limited.

It has been demonstrated that the novel compounds of formula I inhibit neurogenic inflammation which involves the release of neuropeptides from peripheral and central endings of sensory C-fibres. Experimentally this can be demonstrated in animal models of formalin induced pain or paw oedema (Wheeler and Cowan, Agents Actions 1991, 34, 264–269) in which the novel compounds of formula I exhibit a potent inhibitory effect. Compounds of formula I may be used to treat all painful, hyperalgesic and/or inflammatory conditions in which C-fibers play a pathophysiological role by eliciting neurogenic pain or inflammation, i.e.:

Acutely painful conditions exemplified by migraine, postoperative pain, burns, bruises, post-herpetic pain (Zoster) and pain as it is generally associated with acute inflammation; chronic, painful and/or inflammatory conditions exemplified by various types of neuropathy (diabetic, post-traumatic, toxic), neuralgia, rheumatoid arthritis, spondylitis, gout, inflammatory bowel disease, prostatitis, cancer pain, chronic headache, coughing, asthma, chronic pancreatitis, inflammatory slin disease including psoriasis and autoimmune dermnatoses, osteoporotic pain.

Further, it has been demonstrated that the compounds of general formula I improves the glucose tolerance in diabetic ob/ob mice and that this may result from the reduced release of CGRP from peripheral nervous endings. Hence the compounds of general formula I may be used in the treatment of NIDDM as well as ageing-associated obesity. Experimentally this has been demonstrated by the subcutaneous administration of glucose into ob/ob mice with or without previous oral treatment with a compound of general formula I.

The compounds of formula I may be prepared by the following method:

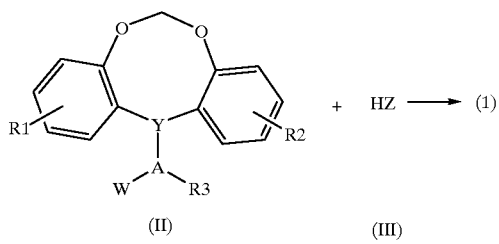

A compound of formula II wherein $R^1$, $R^2$, $R^3$, A, and Y are as defined above and W is a suitable leaving group such as halogen, p-toluene sulphonate or mesylate may be reacted with an azaheterocyclic compound of formula III wherein Z is as defined above. This alkylation reaction may be carried out in a solvent such as acetone, dibutylether, 2-butanone, methyl ethyl ketone, ethyl acetate, tetrahydrofulan (THF) or toluene in the presence of a base e.g. sodium hydride and a catalyst, e.g. an alkali metal iodide at a temperature up to reflux temperature for the solvent used for e.g. 1 to 120 h. If esters have been prepared in which $R^{15}$ is alkoxy, compounds of formula I wherein $R^{15}$ is OH may be prepared by hydrolysis of the ester group, preferably at room temperature in a mixture of an aqueous alkali metal hydroxide solution and an alcohol such as methanol or ethanol, for example, for about 0.5 to 6 h.

Compounds of formula II and III may readily be prepared by methods familiar to those skilled in the art.

Under certain circumstances it may be necessary to protect the intermediates used in the above methods e.g. a compound of formula III with suitable protecting groups. The carboxylic acid group can, for example, be esterified. Introduction and removal of such groups is described in "Protective Groups in Organic Chemistry" J. F. W. McOrnie ed. (New York, 1973).

Pharmacological Methods

I. Formalin Induced Pain or Paw Oedema

Values for in vivo inhibition of formalin induced pain or oedema for the compounds of the present invention were assessed in mice essentially by the method of Wheeler-Aceto and Cowan (Agents Action 1991, 34, 265–269).

About 20 g NMRI female mice were injected 20 ml 1% formalin into the left hind paw. The animals were then placed on a heated (31° C.) table, and the pain response was scored. After 1 h they were killed and bled. Left and right hind paws were removed and the weight difference between the paws was used as indication of the oedema response of the formalin injected paw.

II. Histamin Induced Paw Oedema

Values for in vivo inhibition of histamine induced oedema for the compounds of the present invention were assessed in rats essentially as described by Amann et al. (Europ. J. Pharmacol. 279, 227–231, 1995).

In brief 250–300 g male Sprague-Dawley rats were anaesthetized with pentobarbital sodium, and placed on a 32 degree heated table. Ten minutes later histamine (50 microliter, 3 mg/ml) was injected in the right hind paw and 20 minutes hereafter the paw swelling was determined by water plethysmography (Ugo Basile). Test compounds were administered intraperitoneally at 15 minutes before the anaesthetics.

TABLE 1

| Inhibition of histamine induced oedema at 1 mg/kg | |
|---|---|
| Example no. | % oedema inhibition |
| 2 | 52 |
| 3 | 33 |

III. Reduced Release of CGRP ob/ob female mice, 16 weeks of age, where injected glucose (2 g/kg) subcutaneously. At times hereafter blood glucose was determined in tail venous blood by the glucose oxidase method. At the end of the study the animals were decapitated and trunk blood collected. Immunoreactive CGRP was determined in plasma by radio-immuno-assay. Two groups of animals were used. The one group was vehicle treated, whereas the other group received a compound of formula I via drinking water (100 mg/l) for five days before the test.

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent.

The compounds of formula I may be administered in a pharmaceutically acceptable acid addition salt form or where possible as a metal or a lower alkylammonium salt. Such salt forms exhibit approximately the same order of activity as the free base forms.

This invention also relates to pharmaceutical compositions comprising a compound of formula I or a pharmaceutically acceptable salt thereof and, usually, such compositions also contain a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatine, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

Generally, the compounds of this invention are dispensed in unit dosage form comprising 50–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet which may be prepared by conventional tabletting techniques contains

| Core: | |
|---|---|
| Active compound (as free compound or salt thereof) | 100 mg |
| Colloidal silicon dioxide (Aerosil*) | 1.5 mg |
| Cellulose, microcryst. (Avicel*) | 70 mg |
| Modified cellulose gum (Ac-Di-Sol*) | 7.5 mg |
| Magnesium stearate | |
| Coating: | |
| HPMC | approx. 9 mg |
| *Mywacett* 9-40 T | approx. 0.9 mg |

*Acylated monoglyceride used as plasticizer for film coating.

The route of administration may be any route which effectively transports the active compound to the appropriate or desired site of action, such as oral or parenteral e.g. rectal, transdermal, subcutaneous, intanasal, intramuscular, topical, intravenous, intraurethrai, ophthalmic solution or an ointment, the oral route being preferred.

EXAMPLES

The process for preparing compounds of formula I and preparations containing them is further illustrated in the following examples, which, however, are not to be construed as limiting.

Hereinafter, TLC is thin layer chromatography and $CDCl_3$ is deuterio chloroform and $DMSO-d_6$ is hexadeuterio dimethylsulfoxide. The structures of the compounds are confirmed by either elemental analysis or NMR, where peaks assigned to characteristic protons in the title compounds are presented where appropriate. $^1$H-NMR shifts ($\delta_H$) are given in parts per million (PPM). M.p. is melting point and is given in ° C. and is not corrected. Column chromatography was carried out using the technique described by W. C. Still et al, J. Org. Chem. (1978), 43, 2923–2925 on Merck silica gel 60 (Art. 9385). Compounds used as starting materials are either known compounds or compounds which can readily be prepared by methods known per se.

Example 1
1-(3-(12H-Dibenzo[d,g][1,3]dioxocin-12-ylidene)-1-propyl)-3-piperidinecarboxylic acid hydrochloride

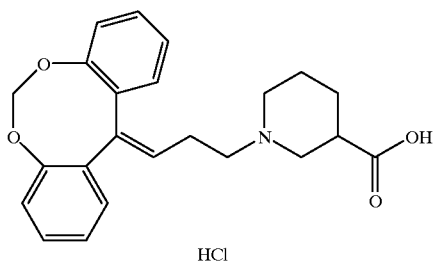

2,2'-Dihydroxybenzophenone (10.0 g, 46.7 mmol) and diiodomethane (13.1 g, 49 mmol) was dissolved in dry dimethylformamide (180 ml). Dried, finely powdered potassium carbonate (9.2 g, 66.7 mmol) was added, and the mixture was heated at 105° C. for 16 h. After cooling to room temperature the reaction mixture was poured into ice water (500 ml). The precipitate was collected by filtration after 0.5 h, washed with water on the filter and dissolved in a mixture of ethanol (80 ml) and 4 N sodium hydroxide (20 ml). The solution was stirred at reflux temperature for 1 h, cooled and diluted with water (300 ml). The formed crystalline precipitate was filtered off, washed with water (50 ml) and dried in vacuo, affording 12H-dibenzo[d,g][1,3]dioxocin-2-one as a solid (9.5 g, 90% yield).

M.p. 93–95° C.

A solution of cyclopropylmagnesium bromide in dry tetrahydrofuran (prepared from cyclopropylbromide (24.2 g, 0.2 mol), magnesium turnings (4.86 g, 0.2 mol) and dry tetrahydrofuran (70 ml) was placed under an atmosphere of nitrogen. A solution of the above ketone (9.05 g, 40 mmol) in dry tetrahydrofuran (50 ml) was added dropwise. The reaction mixture was stirred at 40° C. for 1.5 h, cooled and added to an ice-cold mixture of saturated ammonium chloride (400 ml) and ether (200 ml). The organic layer was separated, the aqueous phase was extracted with ether (50 ml), the combined organic extracts were washed with water (2×100 ml) and brine (50 ml), dried over $MgSO_4$, evaporated in vacuo and stripped with toluene (2×25 ml) to furnish 11.2 g 12-cyclopropyl-12H-dibenzo[d,g][1,3]dioxocin-12-ol.

$^1$H NMR (200 MHz, $CDCl_3$): δ 0.50 (d, 2H); 0.75 (d, 2H); 2.00 (m, 1H); 5.14 (s, 2H); 6.9–7.4 (m, 6H); 7.81 (d, 2H).

To a solution of the above alcohol (6.21 g, 22 mmol) in dry dichloromethane (225 ml) trimethylsilylbromosilane (3.71 g, 24.2 mmol) was added. The reaction mixture was stirred at room temperature for 1 h and poured on an ice-cold saturated sodium hydrogencarbonate solution (75 ml). The organic phase was separated, washed with icewater (2×75 ml) and brine (75 ml), dried over $MgSO_4$ and evaporated in vacuo, which afforded 7.95 g of crude 12-(3-bromo-1-propylidene)-12H-dibenzo[d,g][1,3]dioxocine, which was used in the next step without further purification.

A mixture of the above crude bromide (1.83 g, 5.5 mmol), ethyl 3-piperidinecarboxylate (0.865 g, 5.5 mmol), dried potassium carbonate (2.28 g, 16.5 mmol), sodium iodide (0.82 g, 5.5 mmol) and 2-butanone (25 ml) was heated at reflux temperature for 3 h. After cooling to room temperature, diethyl ether (50 ml) and water (50 ml) was added to the reaction mixture. The organic layer was separated, washed with water (2×50 ml) and made acidic by addition of 2 N hydrochloric acid. The aqueous layer was separated and the organic phase was extracted twice with water (50 ml). The combined aqueous extracts were adjusted to pH 8.5 with a saturated sodium bicarbonate solution and extracted with dichloromethane (2×25 ml). The organic extract was washed with water (50 ml) dried over $MgSO_4$ and evaporated in vacuo, which afforded 1-(3-(12H-dibenzo[d,g][1,3]dioxocin-12-ylidene)-1-propyl)-3-piperidinecarboxylic acid ethyl ester as a foam (1.66 g, 74%).

The above ester (1.66 g, 4.0 mmol) was dissolved in ethanol (20 ml) and 2 N sodium hydroxide (6.6 ml, 13.2 mmol) was added. The mixture was stirred at room temperature for 1.5 h. The ethanol was evaporated in vacuo and the remainder was diluted with water (25 ml). 1 N Hydrochloric acid (17.6 ml) was added and the solution was washed with diethyl ether (25 ml). The aqueous phase was extracted with dichloromethane (3×30 ml). The combined organic extracts were dried over $MgSO_4$ and evaporated in vacuo to afford 1.1 g of the title compound as a foam, which was triturated with ethyl acetate, filtered off and dried.

M.p. 190–92° C., decomp.

Calculated for $C_{23}H_2NO_4$, HCl 0.25 $C_4H_8O_2$: C, 65.82%; H, 6.44%; N, 3.20%; Found: C, 65.76%; H, 6.58%; N, 3.05%.

Example 2
(R)-1-(3-(12H-Dibenzo[d,g][1,3]dioxocin-12-ylidene)-1-propyl)-3-piperidinecarboxylic acid hydrochloride

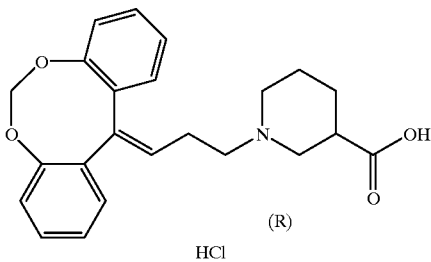

A mixture of 12-(3-bromo-1-propyhdene)12H-dibenzo[d,g,][1,3]dioxocine (7.90 g, 22 mmol, prepared as described in example 1, (R)-3-piperidinecarboxylic acid ethyl ester (L)-tartrate (6.60 g, 22 mmol), dry potassium carbonate (12.2 g, 88 mmol), sodium iodide (3.5 g, 22 mmol) and 2-butanone (100 ml) was heated at reflux temperature for 16 h. After cooling to room temperature, diethyl ether (100 ml) and water (100 ml) was added. The organic layer was separated, washed with water (2×50 ml) and made acidic by addition of 2 N hydrochloric acid. The aqueous layer was separated and the organic phase was extracted twice with water (50 ml).

The combined aqueous extracts were adjusted to pH 8.5 with a saturated sodium bicarbonate solution and extracted with dichloromethane (2×25 ml). The organic extract was washed with water (50 ml) dried over $MgSO_4$ and evaporated in vacuo. The resulting residue (6.21 g) was purified by chromatography on silica gel using a mixture of toluene and ethyl acetate as eluent to give (R)-1-(3-(12H-dibenzo[d,g][1,3]dioxocin-12-ylidene)-1-propyl)-3-piperidinecarboxylic acid ethyl ester as an oil (3.96 g, 41%).

The above ester (3.06 g, 7.5 mmol) was dissolved in ethanol (40 ml) and 2 N sodium hydroxide (12.4 ml, 24.8 mmol) was added. The mixture was stirred at room temperature for 1.0 h. The ethanol was evaporated in vacuo and the remainder was diluted with water (25 ml). The pH was adjusted to 6 by addition of 1 N hydrochloric acid and the solution was washed with diethyl ether (25 ml). The aqueous phase was extracted with dichloromethane (3×30 ml). The combined organic extracts were dried over $MgSO_4$ and evaporated in vacuo to afford 2.75 g of a foam, which was dissolved in tetrahydrofuran (75 ml). Dropwise addition of excess hydrogen chloride in ether afforded the title compound as crystals, which were filtered off and dried (2.65 g, 85%).

M.p. 227–228° C., decomp.

Calculated for $C_{23}H_{25}NO_4$, HCl: C, 66.42%; H, 6.30%; N, 3.37%; Found: C, 66.50%; H, 6.61%; N, 3.14%.

EXAMPLE 3
(R)-1-(3-(12H-Dibenzo[d,g][1,3]dioxocin-12-ylidene)-1-propyl)-3-piperidinecarboxylic acid ethyl ester hydrochloride (R)-1-(3-(12H-dibenzo[d,g][1,3]dioxocin-12-ylidene)-1-propyl)-3-piperidinecarboxylic acid ethyl ester (0.86 g, 2.1 mmol, prepared as described in example 2 was dissolved in tetrahydrofuran (10 ml) and a 2.6 N solution of hydrogen chloride in ether (0.97 ml, 2.52 mmol) was added dropwise. The solution was evaporated in vacuo and the remainder was treated with ether (20 ml). The precipitate was filtered off, washed with ether and dried in vacuo, affording the title compound as a powder.

Calculated for $C_{25}H_{29}NO_4$, HCl, 0.5 $H_2O$: C, 66.29%; H, 6.90%; N, 3.09%; Found: C, 65.97%; H, 7.03%; N, 2.87%.

EXAMPLE 4
1-(3-(12H-Dibenzo[d,g][1,3]dioxocin-12-ylidene)-1-propyl)-4-piperidinecarboxylic acid hydrochloride

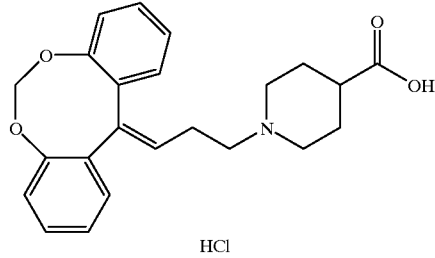

A mixture of 12-(3-bromo-1-propylidene)-12H-dibenzo[d,g][1,3]dioxocine (4.0 g, 12 mmol, prepared as described in example 1, 4-piperidinecarboxylic acid ethyl ester (1.9 g, 12 mmol), anhydrous potassium carbonate (5.0 g) and sodium iodide (0.2 g) in N,N-dimethylformamide (40 ml) was heated at 60–70° C. for 5 h. After cooling, the inorganic salts were filtered off and washed with benzene (40 ml), and the filtrate was diluted with additional benzene (120 ml). The benzene solution was washed with water (3×50 ml), dried over $MgSO_4$ and evaporated in vacuo. The oily residue (4.8 g) was purified by chromatography on silica gel using a mixture of benzene and ethyl acetate as eluent to give 1-(3-(12H-dibenzo[d,g][1,3]dioxocin-12-ylidene)-1-propyl)-4-piperidinecarboxylic acid ethyl ester as an oil (2.3 g, 47%).

The above ester (2.30 g, 5.6 mmol) was dissolved in ethanol (30 ml), a 20% solution of sodium hydroxide (3.5 ml) was added and the mixture was stirred at room temperature for 7 h. The solution was diluted with dichloromethane (240 ml) and acidified with concentrated hydrochloric acid (3 ml). The mixture was washed with water (10 ml), the organic phase was dried over $MgSO_4$ and evaporated in vacuo. The solid residue was washed with acetone, filtered off and dried in vacuo, affording the title compound (1.8 g, 73%).

M.p. 239–245° C.

Calculated for $C_{23}H_{25}NO_4$, HCl, 0.5 $C_2H_5OH$: C, 65.67%; H, 6.66%; Cl, 8.08%; N, 3.19%; Found: C, 65.51%; H, 6.35%; Cl, 8.78%; N, 3.27%.

EXAMPLE 5
(R)-1-(3-(2,10-Dichloro-12H-dibenzo[d,g][1,3]-dioxocin-12-ylidene)-1-propyl)-3-piperidinecarboxylic acid hydrochloride

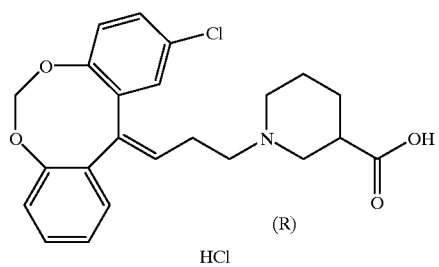

2,2'-Dihydroxy-5,5'-dichlorobenzophenone (12.1 g, 0.042 mol, prepared similarly as described in Journal of the American Chemical Society 77, 543 (1955)) and diiodomethane (11.9 g, 0.044 mol) were dissolved in dry N,N-dimethylformamnide (226 ml). Dried and powdered potassium carbonate (8.3 g) was added and the mixture was heated at 105° C. for 5 h and left overnight at room temperature. The reaction mixture was poured on ice (220 g). The precipitate was collected by filtration after 0.5 h and dissolved in diethyl ether (500 ml). The organic layer was washed with 5% sodium hydroxide (50 ml), dried over $MgSO_4$ and evaporated in vacuo, affording 12 g (96%) of 2,10-dichloro-12H-dibenzo[d,g][1,3]-dioxocin-12-one as a solid.

To a solution of cyclopropylmagnesium bromide in dry tetrahydrofuran (prepared from cyclopropylbromide (15.7 g, 0.130 mol), magnesium turnings (3.15 g, 0.130 mol) and dry tetrahydrofuran (45 ml)), a solution of the above ketone (7.65 g, 0.026 mol) in dry tetrahydrofuran (30 ml) was added over 5 minutes with cooling. The reaction mixture was stirred at 38–42° C. for 3 h, cooled in an ice-bath, and a mixture of saturated ammonium chloride (260 ml) and diethyl ether (130 ml) was added. The reaction mixture was filtered, the organic layer was separated, the aqueous phase was extracted with diethyl ether (35 ml). The combined organic extracts were washed with water (2×70 ml) and brine (70 ml), dried over $MgSO_4$ and evaporated in vacuo. The crude product was purified by column chromatography on silica gel (140 g) using benzene as eluent. This afforded 8.75 g (98%) of 2,10-dichloro-12-cyclopropyl-12H-dibenzo [d,g][1,3]dioxocin-12-ol as a solid. To a solution of the above alcohol (8.75 g, 0.027 mol) in dry dichloromethane (245 ml) trimethylsilyl bromide (4.02 g, 0.026 mol) was added. The reaction mixture was stirred at room temperature for 1 h and poured on an ice cold saturated sodium hydrogencarbonate solution (80 ml). The organic phase was separated, washed with water (2×80 ml) and brine (80 ml), dried over $MgSO_4$ and evaporated in vacuo. This afforded 9.12 g of an oil, which was purified by column chromatography on silica gel (250 g) using a mixture of cyclohexane and benzene (3:1) as eluent. This yielded 6.61 g (61.8%) of 2,10-dichloro-12-(3-bromo-1-propylidene)-12H-dibenzo[d, g][1,3]-dioxocine as an oil which crystallized on standing.

A mixture of the above bromide (3.0 g, 0.0075 mol), (R)-3-piperidinecarboxylic acid ethyl ester tartrate (3.45 g, 0.0112 mol), dried potassium carbonate (10.35 g, 0.075 mol) and dimethylformamide (42 ml) was heated at 60° C. for 12 h. After cooling to room temperature, water (150 ml) and benzene (75 ml) were added. The organic layer was separated, washed with water (3×60 ml), dried over $MgSO_4$ and evaporated in vacuo. The crude oil was purified by column chromatography on silica gel (65 g) using chloroform as eluent. This afforded 1.44 g (40%) of (R)-1-(3-(2, 10-dichloro-12H-dibenzo [d,g][1,3]-dioxocin-12-ylidene)-1-propyl)-3-piperidinecarboxylic acid ethyl ester as an oil.

The above ester (1.44 g, 0.003 mol) was dissolved in ethanol (25 ml) and 4 N sodium hydroxide (3.36 ml, 0.013 mol) was added. The mixture was left at room temperature overnight. Concentrated hydrochloric acid (1.68 ml), followed by dichloromethane (170 ml) were added, the organic layer was separated, dried over $MgSO_4$ and evaporated. Evaporation was repeated with dichloromethane (120 ml) and acetone (20 ml). The oily residue was dissolved in acetone (10 ml), yielding, after 12 h at room temperature, 0.54 g (37%) of the title compound as crystals.

$^1$H NMR (250 MHz, DMSO-$d_6$, $\delta_H$): 7.49 (d, J=2.5 Hz, 1 H); 7.32 (dd, J=2.5 Hz and 8.8 Hz, 1 H);7.26 (dd, J=2.5 Hz and 8.8 Hz, 1 H); 7.19 (d, J=2.5 Hz, 1 H); 7.09 (d, J=8.8 Hz, 1 H); 6.97 (d, J=8.8 Hz, 1 H); 6.09 (t, J=7.2 Hz, 1 H); 5.84 (s, 2 H); 2.43 (q, J=7.2 Hz, 2 H); 3.15 (t, J=7.2 Hz).

Calculated for $C_{23}H_{23}Cl_2NO_2$, HCl, 0.5 $C_3H_6O$: C, 57.26%; H, 5.30%; N, 2.73%; Cl, 20.70%; Found: C, 56.95%; H, 5.31%; N, 2.53%; Cl, 20.75%.

EXAMPLE 6

1-(3-(12H-Dibenzo[d,g][1,3]dioxocin-12-ylidene)-1-propyl)-3-pyrrolidineacetic acid hydrochloride

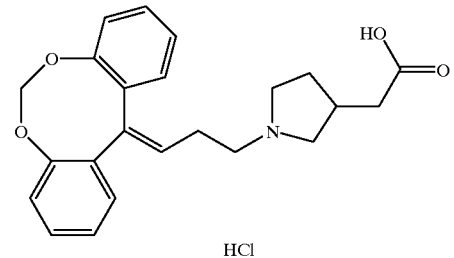

A mixture of 12-(3-bromo-1-propylidene)-12H-dibenzo [d,g][1,3]dioxocine (5.00 g, 15 mmol, prepared as described in example 1, methyl 3-pyrrolidineacetate acetate (3.04 g, 15 mmol), potassium carbonate (6.2 g, 45 mmol) and potassium iodide (2.23 g, 13 mmol) in 2-butanone (70 ml) was heated at reflux temperature for 5 h. The reaction mixture was cooled and water (140 ml) and ether (140 ml) were added. The mixture was vigorously stirred for 5 minutes, the organic layer was separated, washed with water (2×50 ml) and dried over $MgSO_4$. The solvent was evaporated in vacuo and the residue (4.34 g) was submitted to column chromatography on silica gel (100 g) using a mixture of dichloromethane and methanol (10:1) as eluent. This afforded 1.05 g of 1-(3-(12H-dibenzo[d,g][1,3]dioxocin-12-ylidene)-1-propyl)-3-pyrrolidineacetic acid methyl ester.

To a solution of the above ester (0.85 g, 2.1 mmol) in ethanol (16 ml), 20% sodium hydroxide (1.3 ml) was added, the mixture was stirred at room temperature for 2 h and left to stand overnight. The solution was poured into dichloromethane (100 ml), cooled in an ice bath, acidified with 2 N hydrochloric acid and stirred for 10 minutes. Additional water was added (5 ml). The organic layer was dried over $MgSO_4$, partially decolorized with active charcoal and evaporated in vacuo. The hydrochloride of the title compound separated as an amorphous hygroscopic solid (0.64 g, 77%).

M.p. 70–90° C.

$^1$H NMR (250 MHz, $CDCl_3$ )$\delta_H$: 7.15 (m, ~8 H); 5.95 (t, J=7.2 Hz, 1H); 5.85 (s, 2 H) 3.36–1.51 (bm, 13H).

Calculated for $C_{23}H_5NO_4$, HCl, 0.5 $C_2H_6O$. C, 65.67%; H, 6.66%; N, 3.19%; Found: C, 65.79%; H, 6.59%; N, 3.21%.

EXAMPLE 7

1-(3-(2,10-Dichloro-2H-dibenzo[d,g][1,3]dioxocin-12-ylidene)-1-propyl)-3-pyrrolidineacetic acid hydrochloride

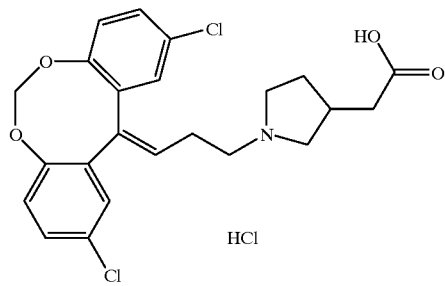

A mixture of 2,10-dichloro-12-(3-bromo-1-propylidene)-12H-dibenzo[d,g][1,3]-dioxocine (4.0 g, 0.01 mol, prepared as described in example 4, 3-pyrrolidinacetic acid methyl ester acetate (2.23 g, 0.011 mol), potassium carbonate (4.5 g, 0.0325 mol) and sodium iodide (1.1 g, 7.3 mmol) in 2-butanone (60 ml) was heated at reflux temperature for 6 h. After cooling to room temperature the reaction mixture was diluted with acetone, filtered and evaporated in vacuo. The crude product was purified by column chromatography on silica gel (200 g), using a mixture of chloroform (95%) and ethanol (5%) as eluent. This afforded 0. 8 g (17.3%) of 1-(3-(2, 10-dichloro-12H-dibenzo[d,g][1,3]dioxocin-12-ylidene)-1-propyl-3-pyrrolidineacetic acid methyl ester as an oil.

To the above ester (0.8 g, 1.78 mmol) in ethanol (11.6 ml) a solution of sodium hydroxide (0.288 g) in water (1.08 ml) was added and the reaction mixture was stirred at room temperature for 16 h. Concentrated hydrochloric acid (1.08 ml) was added followed by dichloromethane (80 ml). After stirring for 10 minutes the organic layer was separated, dried over MgSO$_4$ and evaporated in vacuo. The residue was dissolved in acetone (20 ml) and evaporated. The re-evaporation with acetone was repeated twice. The residue was again dissolved in acetone (40 ml) and left at 0° C. for 4 h. This afforded 300 mg (36%) of the title compound as a solid.

M.p. 183–193° C., decomp.

Calculated for CH,Cl$_2$NO$_4$, HCl: C, 56.98%; H, 4.99%; N, 2.89%; Found: C, 56.92%; H,5.02%; N, 3.16%.

EXAMPLE 8

(R)-1-(2-(12H-Dibenzo[d,g][1,3]dioxocin-12-yloxy)-1-ethyl)-3-piperidinecarboxylic acid acetate

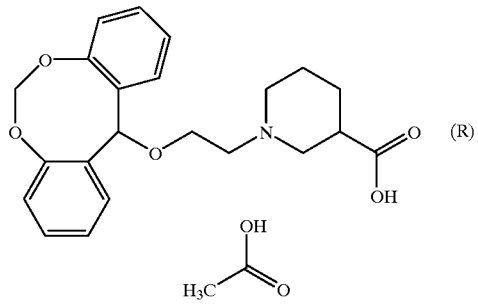

To a suspension of 12H-dibenzo[d,g][1,3]dioxocin-12-one (9.05 g, 40 mmol) in ethanol (140 ml) a solution of sodium borohydride (0.8 g, 21 mmol) in water (5 ml containing 2 drops of 10% sodium hydroxide) was added dropwise at 40° C. and the reaction mixture was stirred at 70° C. for 5 h. Additional solid sodium borohydride (1.0 g, 2.6 mmol) was added in small portions and the reaction mixture was heated to 70° C. for 2 h. The cloudy solution was filtered and the solvent removed in vacuo. Toluene (150 ml) and water (80 ml) were added, the layers were separated, and the aqueous layer was extracted with toluene (50 ml). The combined toluene extracts were washed with water (50 ml), dried over MgSO$_4$ and evaporated in vacuo. The residue (9.03 g), which crystallised after standing was triturated with cyclohexane and filtered off, and the hereby obtained 12H-dibenzo-[d,g][1,3]dioxocin-12-ol was used in next step without further purification.

M.p. 80–90° C.

To a solution of the above alcohol (5.0 g, 22 mmol) in benzene (85 ml) triethylamine (5.5 g, 54 mmol) was added, and a solution of methanesulfonyl chloride (3.2 g, 28 mmol) in benzene (25 ml) was added dropwise at 15–20° C. over 20 minutes under cooling on a cold water bath. After addition, the reaction mixture was stirred for 2 h at room temperature. Water (35 ml) was added, and the organic layer was separated, washed with water (25 ml), dried over MgSO$_4$ and evaporated in vacuo. To the residual oil (5.8 g), anhydrous potassium carbonate (8.6 g, 62 mmol) and 2-bromoethanol (13.6 ml, 191 mmol) were added. The reaction mixture was stirred for 17 h at room temperature, diluted with dichloromethane (60 ml), filtered and evaporated in vacuo. Solid 12-(2-bromoethoxy)-12H-dibenzo[d,g][1,3]dioxocine (5.0 g, 68%) separated from the residue after standing at room temperature and was filtered off and washed with petroleum ether.

M.p. 112–114° C.

A solution of the above bromide (1.7 g, 5 mmol), (R)-3-piperidinecarboxylic acid ethyl ester tartrate (2.1 g, 6.7 mmol) and potassium carbonate (1.1 g, 8 mmol) was stirred for 22 h at room temperature. Inorganic salts were filtered off, and the filtrate was diluted with water (130 ml) and extracted with diethyl ether (2×40 ml). The organic extracts were washed with water (2×20 ml), dried over MgSO$_4$ and evaporated in vacuo. The oily residue, crude (R)-1-(2-(12H-dibenzo[d,g][1,3]-dioxocin-12-yloxy)-1-ethyl)-3-piperidinecarboxylic acid ethyl ester was used in the next step without further purification.

The above ester (1.6 g, 3.9 mmol) was dissolved in ethanol (16 ml) and 20% sodium hydroxide (2.1 ml) was added. The reaction mixture was stirred at room temperature for 18 h, poured into dichloromethane (320 ml) and acidified with concentrated acetic acid (5.3 ml). The organic phase was washed with water (50 ml), dried over MgSO$_4$ and evaporated in vacuo. The oily residue was re-evaporated twice with benzene then triturated with acetone to give crystals of the title compound (0.96 g, 55%).

M.p. 120–28° C.; Calculated for C$_{24}$H$_{29}$NO$_7$: C, 65.00%; H, 6.59%; N, 3.16%. Found: C, 65.21%; H, 6.70%; N, 3.06%.

EXAMPLE 9
(R)-1-(2-(2,10-Dichloro-12H-dibenzo[d,g][1,3]dioxocin-12-yloxy)-1-ethyl)-3-piperidinecarboxylic acid hydrochloride

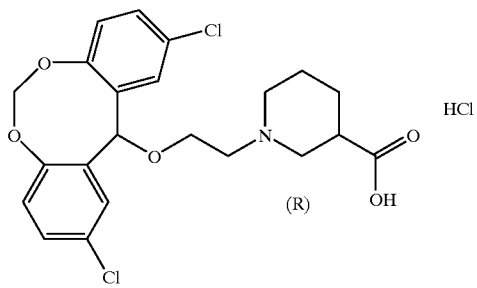

Bis-(5-chloro-2-hydroxyphenyl)methane (25.0 g, 92.9 mmol) was dissolved in N,N-dimethyl formamide (350 ml), and diiodomethane (7.8 ml, 97.5 mmol) and potassium carbonate (18.6 g, 135 mmol) were added. The mixture was heated to 105° C. overnight After cooling, the mixture was poured into icewater (1200 ml). A precipitate was formed immediately. After stirring for 30 minutes, the solid was filtered off and washed with a small amount of water. The solid was suspended in a mixture (80:20) of ethanol and 4 M sodium hydroxide, and the resulting mixture was heated at 80° C. for 1 h. After cooling, the mixture was poured into water (600 ml), and the precipitate was filtered off. After drying, this afforded 2,10-dichloro-12H-dibenzo[d,g][1,3]-dioxocine (24.8 g, 95%), which was used for further reaction without purification.

The above dioxocine (7.7 g, 27 mmol) and N-bromosuccinimide (5.4 g, 30 mmol) were suspended in tetrachloromethane (100 ml). Azobisisobutyronitrile (50 mg) was added and the mixture was heated at reflux temperature. During the first.7 h, every second hour, portions of more azobisisobutyronitrile (50 mg) were added. Heating was continued overnight. Two additional portions of azobisisobutyronitie (50 mg) were then added and heating at reflux temperature was continued for 24 h in total. After cooling, the reaction mixture was filtered and evaporated. Dichloromethane (10 ml) and diethyl ether (15 ml) were added and the solid was filtered off, affording after drying 12-bromo-2,10-dichloro-12H-dibenzo[d,g][1,3]dioxocine (3.37g, 11%).

The above bromide (3.37 g, 9.36 mmol) was mixed with 2-bromoethanol (8.0 ml, 110 mmol) and potassium carbonate (3.9 g, 28 mmol). The mixture was starred for 1 h at room temperature. Dichioromethane (10 ml) was added to dilute the mixture, and stirring was continued overnight at room temperature. The mixture was heated at 120° C. for 24 h. After cooling, the mixture was evaporated, and ethyl acetate (100 ml) and water (100 ml) were added. The phases were separated and the organic phase was washed with water (100 ml). The combined aqueous phases were extracted with ethyl acetate (100 ml). The organic extracts were dried (MgSO$_4$) and evaporated to give crude 12-(2-bromoethoxy)-2,10-dichloro-12H-dibenzo[d,g][1,3]dioxocine (4.34 g). The product was used for further reaction without purification.

The above bromoethoxy compound (4.25 g, 10.5 mmol) was suspended in dimethyl sulfoxide (50 ml). (R)-3-Piperidinecarboxylic acid ethyl ester tartrate (4.1 g, 13.7 mmol) and potassium carbonate (3.2 g, 23 mmol) were added. The reaction mixture was stirred at 50° C. overnight. After cooling and filtration, water (250 ml) was added and the mixture was extracted with diethyl ether (2×100 ml). The organic extracts were washed with water (75 ml), dried (MgSO$_4$) and evaporated. The residual oil was purified by column chromatography on silica gel (600 ml) using a mixture of heptane and ethyl acetate (2:1) as eluent. This afforded (R)-1-(2-(2,10-dichloro-12H-dibenzo[d,g][1,3]dioxocin-12-yloxy)-1-ethyl)-3-piperidinecarboxylic acid ethyl ester (2.0 g, 40%) as an oil.

The above ester (0.78 g, 1.62 mmol), dissolved in a solution of sodium hydroxide (0.54 g, 13.5 mmol) in ethanol (40 ml) and water (5 ml) was stirred at room temperature for 3.5 h. The pH of the mixture was adjusted to 4 by addition of 1 N hydrochloric acid (14 ml). The mixture was extracted with dichloromethane (2×60 ml), the combined organic phases were washed with brine (75 ml), dried over MgSO$_4$ and the solvent was removed in vacuo. The residue was stirred with acetone (10 ml) for 2.5 h, the solid product was filtered off and dried, affording the title compound ( 0.56 g, 71%).

M.p. 218–220° C.; Calculated for $C_{23}H_{23}Cl_2NO_5$, HCl: C, 54.06%; H, 4.95%; N, 2.87%; Found: C, 53.9%; H, 4.8%; N, 2.6%.

EXAMPLE 10
(R)-1-(3-(2-Chloro-12H-dibenzo[d,g,][1,3,6]dioxazocin-12-yl)-1-propyl)-3-piperidinecarboxylic acid hydrochloride

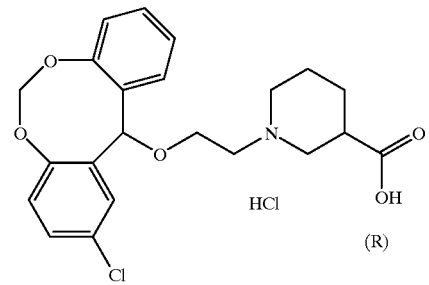

A suspension of 2-chloro-2H-dibenzo[d,g][1,3,6]dioxazocine (10.65 g, 43 mmol, prepared as described in Journal of Molecular Structures, 131, 1985, 131–140) and 3-chloropropionyl chloride (6.55 g, 51.6 mmol) in dry toluene (100 ml) was heated at reflux temperature for 5 h. After cooling to room temperature, the reaction mixture was washed with a saturated solution of sodium bicarbonate (50 ml). The organic layer was dried (MgSO$_4$), and evaporated in vacuo, which afforded 2-chloro-12-(3-chloropropionyl)-12H-dibenzo[d,g][1,3,6]dioxazocine (12.9 g, 88%).

A predried flask with lithium aluminium hydride (3.0 g, 79 mmol), suspended in dry tetrahydrofutran (80 ml), was cooled in an ice bath and concentrated sulphuric acid (3.87 g, 39.5 mmol) was added dropwise at a rate to maintain a temperature <12° C. The solution was stired at room temperature for 1.5 h. A solution of the above chloride (12.8 g, 37.8 mmol) in dry tetraydrofuran (80 ml) was added dropwise and stirring was continued for 2 h. The reaction was quenched by careful addition of ethyl acetate (100 ml) followed by water (5.7 ml). Filtration of the mixture and evaporation of the filtrate in vacuo afforded 2-chloro-12-(3-chioropropyl)-12H-dibenzo[d,g][1,3,6]dioxazocine as a foam.

A mixture of the above crude chloride (1.14 g, 3.5 mmol), (R)-3-piperidinecarboxylic acid ethyl ester (L)-tartrate (1.05 g, 3.5 mmol), dried potassium carbonate (1.94 g, 14 mmol), sodium iodide (0.53 g, 3.5 mmol) and 2-butanone (15 ml) was heated at reflux temperature for 60 h. The reaction mixture was filtered, the filtrate washed with 2-butanone (10 ml) and the combined filtrates evaporated in vacuo. The crude product was purified by column chromatography on silica gel using a mixture of ethyl acetate and heptane (1:3) containing triethylamine (2.5%) as eluent. This afforded the product, (R)-1-(3-(2-chloro-2H-dibenzo[d,g][1,3,6]dioxazocin-12-yl)-1-propyl)-3-piperidinecarboxylic acid ethyl ester (0.77 g, 49 ) as an oil.

The above ester (0.77 g, 1.73 mmol) was dissolved in ethanol (7.5 ml) and 2 N sodium hydroxide (2.86 ml, 5.71 mmol) was added. The mixture was stirred at room temperature for 16 h. The ethanol was evaporated in vacuo and the remainder was diluted with water (25 ml). pH was adjusted to 6 by addition of 6 N hydrochloric acid and the aqueous solution was extracted with dichloromethane (3×15 ml). The combined organic extracts were dried over $MgSO_4$ and evaporated in vacuo. The remainder was dissolved in tetrahydrofuran (15 ml) and 2.5 N hydrogen chloride in ether (0.59 ml, 1.47 mmol) was added dropwise. Ether (30 ml) was added and the mixture was stirred for 3 h, the precipitate was filtered off and dried, to afford 0.53 g (68%) of the title compound as a powder.

M.p. 177–180° C.; Calculated for $C_{22}H_{25}ClN_2O_4$, HCl: C, 58.28%; H, 5.78%; N, 6.18%; Found: C, 58.3%; H, 5.9%; N, 6.1%.

EXAMPLE 11

1-(3-(12H-Dibenzo[d,g][1,3,6]dioxazocin-12-yl)-1-propyl)-4-piperidinecarboxylic acid hydrochloride

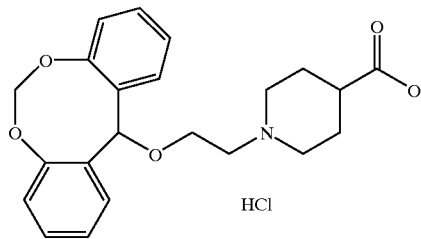

N-(2-Hydroxyphenyl)formamide (16.0 g, 130 mnol) was dissolved in 99.9% ethanol (65 ml). Sodium methoxide 7.0 g, 130 mnol) was suspended in 99.9% ethanol (70 ml) and added dropwise over 30 minutes. The resulting mixture was stirred for 30 minutes. 1-Bromo-2-chloromethoxybenzene (26.1 g, 118 mmol, synthesis described in J. Heterocycl. Chem., 11, 1974, 331–337) was added dropwise over 15 minutes. The reaction mixture was stirred for 2.5 h at room temperature, heated at reflux temperature for 2 h, and stirred at room temperature overnight. The mixture was filtered and evaporated. The residue was dissolved in toluene (500 ml) and washed with a saturated sodium carbonate solution (2×200 ml). The organic phase was dried ($MgSO_4$) and evaporated. The residue was suspended in ethanol (40 ml), filtered and washed with ethanol (3×10 ml). After drying, this afforded the product, N-(2-(2-bromophenoxymethoxy)phenyl)formamide (14.1 g, 37%).

The above formamide (6.8 g, 21 mmol) was suspended in Dowtherm (75 ml), and potassium carbonate (3.9 g, 28 mmol) was added, followed by copper (1.1 g, 17 mmol) and copper bromide (1.5 g, 11 mmol). The reaction mixture was heated at 180° C. overnight. After cooling, the mixture was filtered, and the filter cake was washed with dichloromethane. Dowtherm and solvent was distilled off, and ethanol (200 ml) was added to the residue, which was left overnight. 4 M Sodium hydroxide (14 ml) was added, and the mixture was heated at reflux temperature for 1 h. After cooling, the mixture was filtered and evaporated. The residue was suspended in ethyl acetate (200 ml) and water (100 ml). The organic phase was washed with water (2×75 ml). The aqueous phases were extracted with ethyl acetate (100 ml). The combined organic extracts were evaporated. The residue was suspended in warm cyclohexane (100 ml), and left cooling under stirring. The precipitated solid was filtered off, affording after drying the product 12H-dibenzo[d,g][1,3,6]dioxazocine (4.57 g, 50%).

The above dioxazocine (4.0 g, 19 mmol) was dissolved in dry N,Ndirethylformamide (150 ml). Sodium hydride (1.13 g, 28 mmol, 60% dispersion in oil) was added in portions, and the resulting mixture was stirred for 30 minutes at room temperature. 1-Bromo-3-chloropropane (4.6 ml, 47 mmol) was slowly added dropwise, and the reaction mixture was stirred at room temperature overnight. More sodium hydride (0.56 g, 14 rnmol) was added, and stirring was continued for 6 h. More sodium hydride (0.56 g, 14 mmol) was added, and stirring was continued overnight. Ammonium chloride (3.2 g) was added, and the mixture was stirred for 30 minutes. Water was added (300 ml), and the mixture was extracted with dichloromethane (2×250 ml). The organic extracts were dried ($MgSO_4$) and evaporated. The residue was purified by column chromatography on silica gel using a mixture of heptane and ethyl acetate (6:1) as eluent. This afforded the product, 12-(3-chloropropyl)-12H-dibenzo[d,g][1,3,6]dioxazocine (2.18 g, 40%).

The above chloride (1.0 g, 3.5 mmol) and potassium iodide (3.7 g, 22 mmol) in methyl ethyl ketone (110 ml) was heated at reflux temperature for 4 h. 4-Piperidinecarboxylic acid ethyl ester (0.8 g, 5.2 mmol) was dissolved in methyl ethyl ketone (5 ml) and added, followed by potassium carbonate (1.2 g, 8.6 mmol). The reaction mixture was heated at reflux temperature for 48 h. After cooling, the mixture was filtered, the filter cake was washed with methyl ethyl ketone, and the filtrate was evaporated. The residual oil was purified by column chromatography on silica gel (500 ml) using ethyl acetate as eluent. This afforded 1-(3-(12H-dibenzo[d,c][1,3,6]dioxazocin-12-yl)-1-propyl)-4piperidinecarboxylic acid ethyl ester (0.80 g, 57%) as an oil.

The above ester (0.50 g, 1.22 mmol), dissolved in a solution of sodium hydroxide (0.24 g, 6 mmol) in ethanol (30 ml) and water (3 ml) was stirred at room temperature for 3 h. The pH of the mixture was adjusted to 3 by addition of 1 N hydrochloric acid (5 ml). The mixture was extracted with dichloromethane (2×40 ml), the combined organic phases were washed with brine (50 ml), dried over $MgSO_4$ and the solvent was removed in vacuo. The residue was triturated with acetone (20 ml), the solid product was filtered off and dried, affording the title compound in quantitative yield (0.52 g).

M.p. 180–187° C.; Calculated for $C_{22}H_{26}N_2O_4$, HCl, 1.25 $H_2O$: C, 59.85%; H, 6.74%; N, 6.35%; Found: C, 59.85%; H, 6.60%; N, 6.00%.

What is claimed is:

1. A compound of formula I

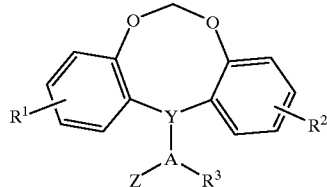

(I)

wherein

R[1] and R[2] independently are hydrogen, halogen, trifluoromethyl, hydroxy, $C_{1-6}$-alkyl or $C_{1-6}$-alkoxy; and R[3] is hydrogen or $C_{1-3}$-alkyl; and A is $C_{1-3}$-alkylene; and Y is $\underline{C}$H—CH2—, $\underline{C}$=CH—, $\underline{C}$H—O— or $\underline{C}$=N—, CH—$\underline{C}$H$_2$—, C=$\underline{C}$H—, CH—O— or C=N—, wherein only the underscored atom participates in the ring system; and Z is

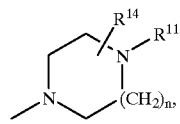

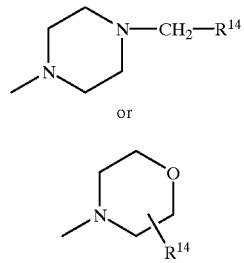

or wherein n is 1 or 2; R[11] is hydrogen or $C_{1-6}$-alkyl; R[14] is —(CH$_2$)$_m$OH or —(CH$_2$)$_t$COR[15]

wherein m is 0, 1, 2, 3, 4, 5 or 6, t is 0 or 1, and R[15] is —OH, NH$_2$, —NHOH or $C_{1-6}$-alkoxy; or a pharmaceutically acceptable salt thereof.

2. A compound of claim 1, wherein R[1] and R[2] independently are hydrogen or halogen.

3. A compound of claim 1, wherein R[14] is —(CH$_2$)$_t$COR[15] wherein t is 0 or 1 and wherein R[15] is —OH.

4. A pharmaceutical composition comprising as an active component a therapeutically effective amount of a compound of claim 1 together with a pharmaceutically acceptable carrier or diluent.

5. The pharmaceutical composition of claim 4, comprising between 0.5 mg and 1000 mg of the compound.

* * * * *

UNITED STATES PATENT AND TRADEMARK OFFICE
CERTIFICATE OF CORRECTION

PATENT NO. : 6,017,915  
DATED : January 25, 2000  
INVENTOR(S) : Königovà et al.

Page 1 of 1

It is certified that error appears in the above-identified patent and that said Letters Patent is hereby corrected as shown below:

Column 19
Line 23, claim 1, delete "CH-CH$_2$-, C=CH-. CH-0– or C=N-"

Signed and Sealed this

Ninth Day of October, 2001

Attest:

NICHOLAS P. GODICI  
Attesting Officer     Acting Director of the United States Patent and Trademark Office